United States Patent
Corr et al.

(10) Patent No.: US 10,258,569 B2
(45) Date of Patent: *Apr. 16, 2019

(54) PHARMACEUTICAL COMPOSITIONS

(71) Applicant: MEXICHEM AMANCO HOLDINGS S.A. DE C.V., Tlalnepantla, Estado De Medico C.P. (MX)

(72) Inventors: Stuart Corr, Cheshire (GB); Timothy James Noakes, Flintshire (GB)

(73) Assignee: MEXICHEM AMANCO HOLDINGS S.A. DE C.V. (MX)

( * ) Notice: Subject to any disclaimer, the term of this patent is extended or adjusted under 35 U.S.C. 154(b) by 0 days.

This patent is subject to a terminal disclaimer.

(21) Appl. No.: 15/270,519

(22) Filed: Sep. 20, 2016

(65) Prior Publication Data

US 2017/0007701 A1 Jan. 12, 2017

Related U.S. Application Data

(63) Continuation of application No. 14/117,340, filed as application No. PCT/GB2012/051059 on May 11, 2012, now abandoned.

(30) Foreign Application Priority Data

May 13, 2011 (GB) .................................. 1108039.7

(51) Int. Cl.
| | | |
|---|---|---|
| A61K 47/06 | (2006.01) | |
| A61K 9/12 | (2006.01) | |
| A61K 47/10 | (2017.01) | |
| A61K 9/00 | (2006.01) | |
| A61K 31/56 | (2006.01) | |
| A61K 31/573 | (2006.01) | |

(52) U.S. Cl.
CPC .............. *A61K 9/124* (2013.01); *A61K 9/008* (2013.01); *A61K 31/56* (2013.01); *A61K 31/573* (2013.01); *A61K 47/06* (2013.01); *A61K 47/10* (2013.01)

(58) Field of Classification Search
CPC ........ A61K 9/124; A61K 47/10; A61K 9/008; A61K 31/56; A61K 31/573; A61K 47/06
See application file for complete search history.

(56) References Cited

U.S. PATENT DOCUMENTS

| | | | |
|---|---|---|---|
| 5,439,670 A | 8/1995 | Purewal et al. | |
| 5,776,432 A | * 7/1998 | Schultz | .................. A61K 9/008 424/45 |
| 6,103,266 A | 8/2000 | Tapolsky et al. | |
| 6,413,497 B1 | 7/2002 | Weil et al. | |
| 6,461,591 B1 | 10/2002 | Keller et al. | |
| 6,475,467 B1 | 11/2002 | Keller et al. | |
| 7,105,152 B1 | 9/2006 | Schultz et al. | |

FOREIGN PATENT DOCUMENTS

| | | |
|---|---|---|
| CN | 1296814 A | 5/2001 |
| EP | 0 372 777 A2 | 11/1989 |
| EP | 0 653 204 A2 | 11/1989 |
| EP | 0 995 434 A2 | 11/1989 |
| EP | 2 072 051 A1 | 6/2003 |
| GB | 2 392 915 A | 3/2004 |
| WO | WO 91/11173 | 8/1991 |
| WO | WO 96/19198 | 6/1996 |
| WO | WO 96/32151 | 10/1996 |
| WO | WO 99/16422 | 4/1999 |
| WO | WO-9916422 A1 * | 4/1999 |
| WO | WO 99/65460 | 12/1999 |
| WO | WO 2005/034911 A1 | 4/2005 |
| WO | WO 2006/004646 A1 | 1/2006 |
| WO | WO 2007/020204 A2 | 2/2007 |
| WO | WO 2011/023734 A1 | 3/2011 |
| WO | WO 2012/093252 A1 | 7/2012 |

OTHER PUBLICATIONS

Michael H. Abraham, et al, Solvation Properties of Refrigerants, and the Estimation of Their Water-Solvent and Gas-Solvent Partitions, 180 Fluid Phase Equil. 180 (Year: 2001).*
Tim Noakes, "Medical aerosol propellants," Elsevier, Journal of Fluorine Chemistry, 118 (2002) pp. 35-45, Cheshire, UK.
International Preliminary Report on Patentability for Int'l Application No. PCT/GB2012/051059, 4 pgs., date of completion Mar. 3, 2013.
International Search Report for Int'l Application No. PCT/GB2012/051059, 5 pgs., date of completion Aug. 23, 2012.
International Search Report and the Written Opinion of the International Searching Authority for Int'l Application No. PCT/GB2012/051059, 11 pgs., dated Sep. 6, 2012.

\* cited by examiner

*Primary Examiner* — Sean M Basquill
(74) *Attorney, Agent, or Firm* — Brinks Gilson & Lione; Jonathan M. Hartley

(57) ABSTRACT

A pharmaceutical solution for a medication delivery apparatus, especially a metered dose inhaler, is described. The pharmaceutical solution comprises: (a) a liquefied propellant component consisting essentially of and preferably consisting entirely of 1,1-difluoroethane (R-152a); (b) ethanol; and (c) a drug component dissolved in the propellant/ethanol mixture consisting of at least one drug selected from the group consisting of beclomethasone dipropionate (BDP) and fluticasone propionate (FP).

13 Claims, 2 Drawing Sheets

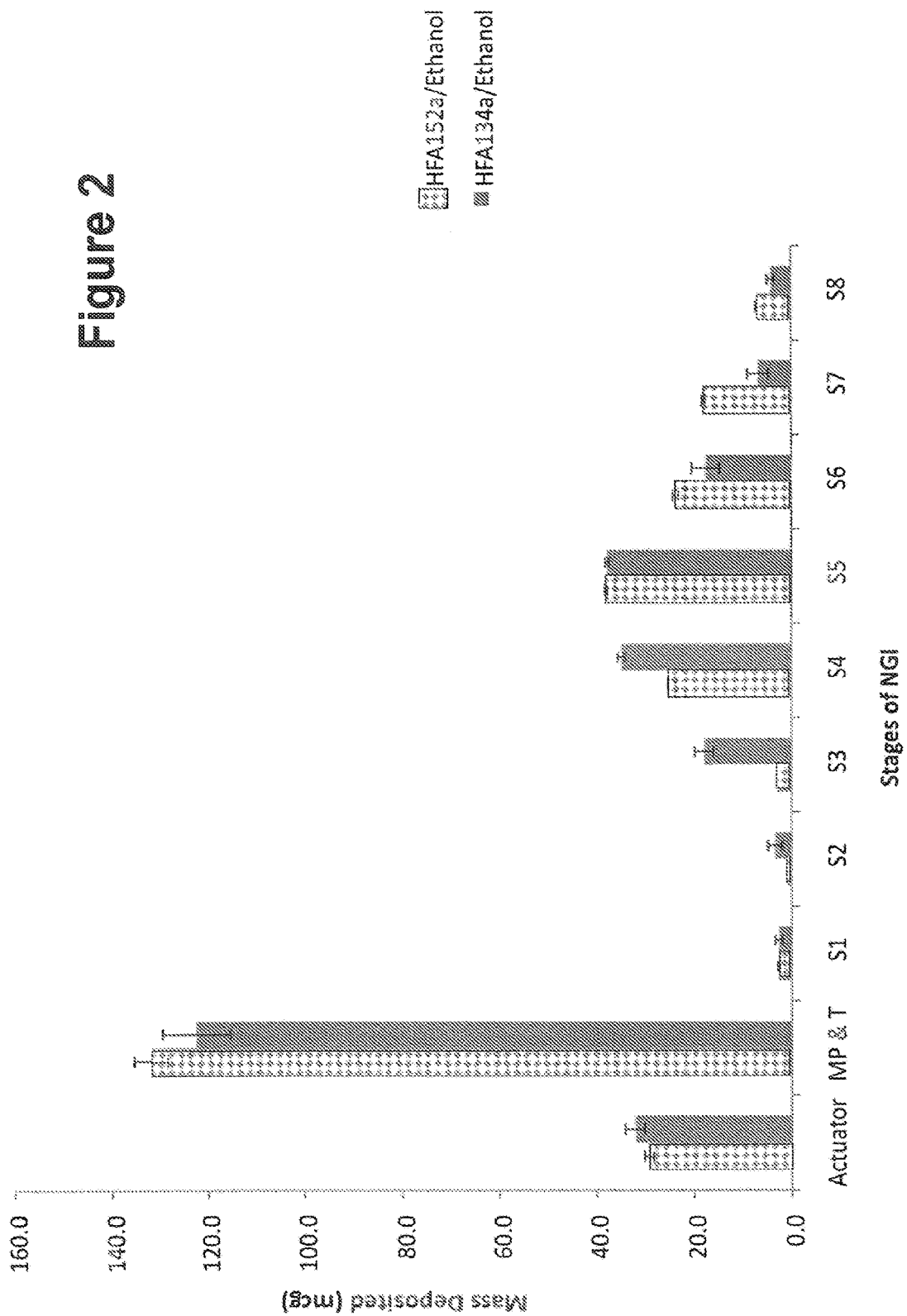

PHARMACEUTICAL COMPOSITIONS

RELATED APPLICATIONS

This application is a continuation application of U.S. application Ser. No. 14/117,340, filed May 12, 2014 which is the U.S. National Phase under 35 U.S.C. § 371 of International Application No. PCT/GB2012/051059, filed May 11, 2012, designating the United States and published in English on Nov. 22, 2012, as WO 2012/156711, which claims priority to United Kingdom Application No. 1108039.7, filed May 13, 2011, which is incorporated by reference in its entirety.

TECHNICAL FIELD

The present invention relates to a pharmaceutical composition comprising a drug, 1,1-difluoroethane (R-152a) propellant and ethanol that is suitable for delivering the drug, especially from a pressurised aerosol container using a metered dose inhaler (MDI).

BACKGROUND

MDIs are the most significant type of inhalation drug delivery system and are well known to those skilled in the art. They are designed to deliver, on demand, a discrete and accurate amount of a drug to the respiratory tract of a patient using a liquefied propellant in which the drug is dissolved, suspended or dispersed. The design and operation of MDIs is described in many standard textbooks and in the patent literature. However, they all comprise a pressurised container that holds the drug formulation, a nozzle and a valve assembly that is capable of dispensing a controlled quantity of the drug through the nozzle when it is activated. All of these components are typically located in a housing that is equipped with a mouth piece. The drug formulation will comprise a propellant, in which the drug is dissolved, suspended or dispersed, and may contain other materials such as co-solvents, surfactants and preservatives.

In order for a propellant to function satisfactorily in MDIs, it needs to have a number of properties. These include an appropriate boiling point and vapour pressure so that it can be liquefied in a closed container at room temperature but develop a high enough pressure when the MDI is activated to deliver the drug as an atomised formulation even at low ambient temperatures. Further, the propellant should be of low acute and chronic toxicity and have a high cardiac sensitisation threshold. It should have a high degree of chemical stability in contact with the drug, the container and the metallic and non-metallic components of the MDI device, and have a low propensity to extract low molecular weight substances from any elastomeric or other polymeric materials in the MDI device. The propellant should also be capable of maintaining the drug in a homogeneous solution, in a stable suspension or in a stable dispersion for a sufficient time. When the drug is in suspension in the propellant, the density of the liquid propellant is desirably similar to that of the solid drug in order to avoid rapid sinking or floating of the drug particles in the liquid. Finally, the propellant should not present a significant flammability risk to the patient in use. In particular, it should form a non-flammable or low flammability mixture when mixed with air in the respiratory tract.

Dichlorodifluoromethane (R-12) possesses a suitable combination of properties and was for many years the most widely used MDI propellant, often blended with trichlorofluoromethane (R-11). Due to international concern that fully and partially halogenated chlorofluorocarbons (CFCs), such as dichlorodifluoromethane and trichlorofluoromethane, were damaging the earth's protective ozone layer, many countries entered into an agreement, the Montreal Protocol, stipulating that their manufacture and use should be severely restricted and eventually phased out completely. Dichlorodifluoromethane and trichlorofluoromethane were phased out for refrigeration use in the 1990's, but are still used, to some extent, in the MDI sector as a result of an essential use exemption in the Montreal Protocol.

1,1,1,2-tetrafluoroethane (R-134a) was introduced as a replacement refrigerant and MDI propellant for R-12. 1,1,1,2,3,3,3-heptafluoropropane (R-227ea) was also introduced as a replacement for R-12 in the fire control (e.g. computer suites) and MDI sectors and is sometimes blended with R-134a for these applications.

Although R-134a and R-227ea have low ozone depletion potentials (ODPs), they have global warming potentials (GWPs), 1430 and 3220 respectively, that are now considered to be too high by some regulatory bodies, especially for dispersive uses when they are released into the atmosphere.

One industrial area that has received particular attention recently has been the automotive air-conditioning sector where the use of R-134a has come under regulatory control as a result of the European F-Gas Regulations. Industry is developing a number of possible alternatives to R-134a in automotive air conditioning and other applications that have a low greenhouse warming potential (GWP) as well as a low ozone depletion potential (ODP). Many of these alternatives include hydrofluoropropenes, especially the tetrafluoropropenes such as 2,3,3,3-tetrafluoropropene (R-1234yf) and 1,3,3,3-tetrafluoropropene (R-1234ze).

Although the proposed alternatives to R-134a have a low GWP, the toxicological status of many of the components, such as certain of the fluoropropenes, is unclear and they are unlikely to be acceptable for use in the MDI sector for many years, if at all.

There are also other problems with R-134a and R-227ea. Most pharmaceutical actives for treating respiratory disorders, such as asthma, tend not to dissolve well in either R-134a or R-227ea and have to be handled as suspensions in the propellant. Drug suspensions give rise to a number of problems, such as nozzle blockage, agglomeration and sedimentation, the latter problem making it essential to shake the MDI thoroughly before use to ensure that the drug is evenly distributed in the propellant. Furthermore, if the pharmaceutical active settles quickly following re-suspension in the propellant, as is often the case, then the propellant/drug composition must be delivered from the MDI shortly after shaking in order to ensure that the dose that is delivered contains an effective concentration of the pharmaceutical active.

The problem of poorly dissolving drugs has been addressed by including a carrier solvent in the composition in which the drug is soluble, such as ethanol, and/or by adding a surfactant to the composition to produce a more stable suspension. However, neither of these solutions is ideal. In particular, they can tend to impair the efficiency of the atomisation process and the quality of the aerosol spray that is delivered from the MDI. For example, carrier solvents such as ethanol can tend to result in a coarse spray having droplet sizes that are too large for acceptable penetration into the deep bronchiole passages of the lung. Further, high levels of ethanol can have unacceptable irritancy to the mouth and throat, especially with younger users. Clearly it would be advantageous to use the minimum levels of ethanol required in order to produce an acceptable solution formulation.

There is a need for a MDI aerosol formulation that has a reduced GWP in comparison with R-134a and R-227ea, that has acceptable flammability and toxicity performance and which forms stable suspensions or solutions with a range of pharmaceutical actives and with reduced irritancy.

SUMMARY

According to a first aspect, the present invention provides for the use of a propellant consisting essentially of and preferably consisting entirely of 1,1-difluoroethane (R-152a) in a pharmaceutical composition comprising a drug, the propellant and ethanol in order to reduce the amount of ethanol required for dissolving the drug in the pharmaceutical composition compared to the amount that would be needed if 1,1,1,2-tetrafluoroethane (R-134a) is used as the propellant.

According to a second aspect, the present invention provides for the use in a pharmaceutical composition comprising a drug, a propellant and ethanol that is designed to be delivered using a medication delivery device and especially a metered dose inhaler of a propellant consisting essentially of and preferably consisting entirely of 1,1-difluoroethane (R-152a) in order to reduce the amount of ethanol required to dissolve the drug in the pharmaceutical composition compared to the amount that would be needed if 1,1,1,2-tetrafluoroethane (R-134a) is used as the propellant.

According to a third aspect, the present invention provides for the use in a medication delivery apparatus, especially a metered dose inhaler, that contains a pharmaceutical composition comprising a drug, a propellant and ethanol of a propellant consisting essentially of and preferably consisting entirely of 1,1-difluoroethane (R-152a) to reduce the amount of ethanol required to dissolve the drug in the pharmaceutical composition compared to the amount that would be needed if 1,1,1,2-tetrafluoroethane (R-134a) is used as the propellant.

According to a fourth aspect of the present invention, there is provided a pharmaceutical solution for a medication delivery apparatus, especially a metered dose inhaler, comprising:
(a) a liquefied propellant component consisting essentially of and preferably consisting entirely of 1,1-difluoroethane (R-152a);
(b) ethanol; and
(c) a drug component dissolved in the propellant/ethanol mixture consisting of at least one drug selected from the group consisting of beclomethasone dipropionate (BDP) and fluticasone propionate (FP).

BRIEF DESCRIPTION OF THE DRAWINGS

FIG. 2 shows in vitro aerosolization performance of beclomethasone dipropionate (250 µg) solutions prepared in (i) R152a and ethanol (2 w/w) and (ii) R-134a and ethanol (4% w/w).

DETAILED DESCRIPTION

Figure 1:
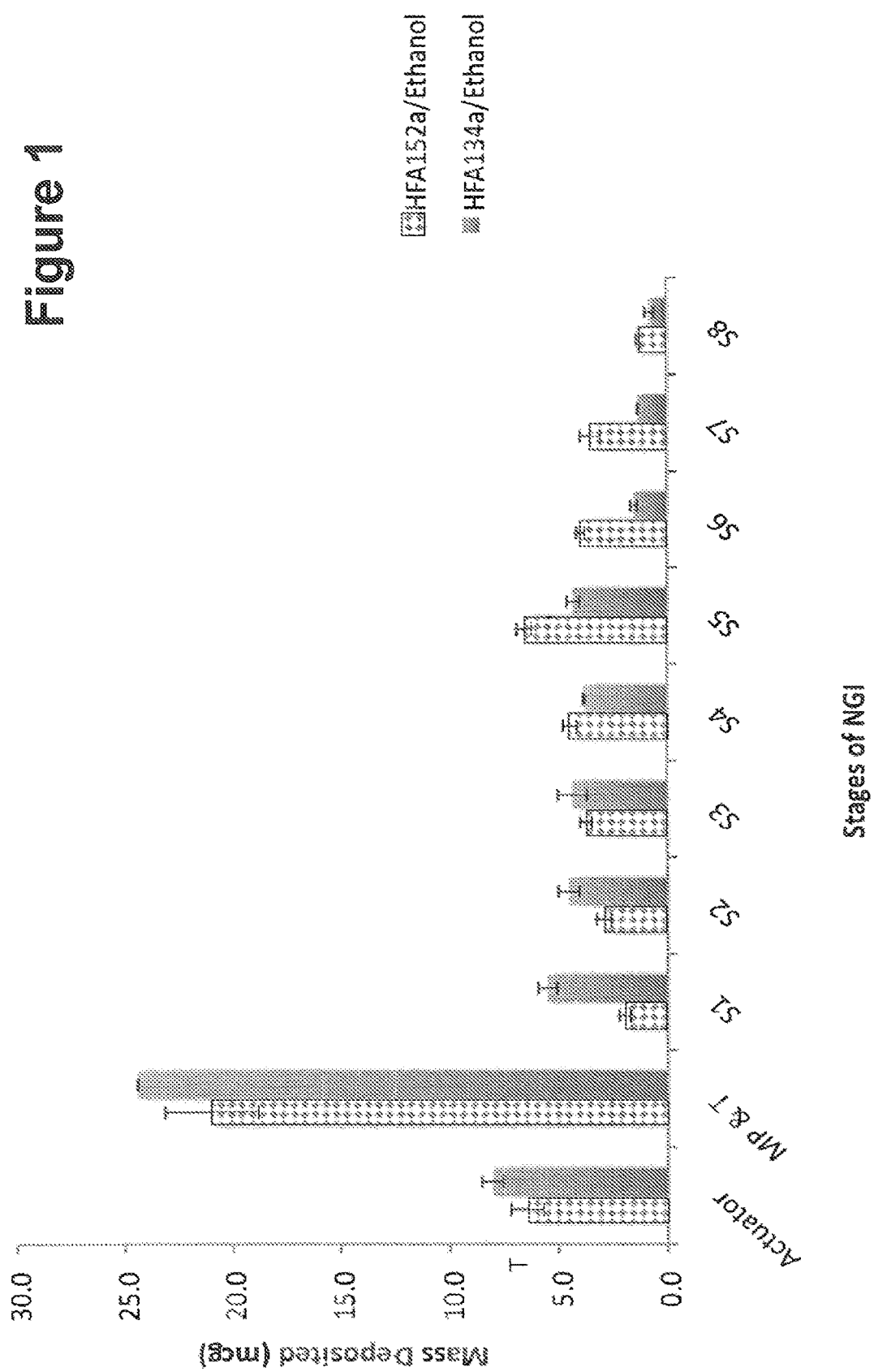
FIG. 1 shows in vitro aerosolization performance of fluticasone propionate (50 µg) solutions prepared in (i) R152a and ethanol (5% w/w) and (ii) R-134a and ethanol (13% w/w).

For the avoidance of doubt, in the pharmaceutical solution of the present invention, the propellant component is that component which comprises all the compounds in the solution that can function as a propellant. Similarly, the drug component is that component which comprises all the compounds in the solution that can function as a medicament. Thus, the only propellants and drugs in the pharmaceutical solutions of the invention are those that make up the propellant component and the drug component respectively.

The propellant component of the pharmaceutical solution of the invention consists essentially of and preferably consists entirely of 1,1-difluoroethane (R-152a). By the term "consists essentially of" we mean that at least 90 weight %, preferably at least 95 weight %, more preferably at least 98 weight % and especially at least 99 weight % of the propellant component is 1,1-difluoroethane (R-152a). All percentages are based on the total weight of the propellant composition.

The solubility of beclomethasone dipropionate (BDP) and fluticasone propionate (FP) in the R-152a/ethanol mixture will obviously vary with temperature, with each drug becoming progressively less soluble as the temperature is lowered. However, in the pharmaceutical solutions of the present invention, the beclomethasone dipropionate and fluticasone propionate can remain fully dissolved in the R-152a/ethanol mixture at the lower temperatures at which MDIs have to work of 5° C.

It will be appreciated that the term "consists essentially of" does allow for the presence of an additional propellant in the propellant component, such as an additional hydrofluorocarbon or hydrocarbon propellant, e.g. selected from R-227ea, R-134a, propane, butane, isobutane, dimethyl ether and R-32 (difluoromethane). However, and as explained above, the propellant component will normally consist entirely of 1,1-difluoroethane (R-152a).

The pharmaceutical solutions of the present invention are designed, particularly, to be contained in a pressurised aerosol canister to be delivered using a MDI.

Conveniently, the pharmaceutical solutions of the invention have a GWP less than 1300, conveniently less than 1000, more conveniently less than 800. Preferred solutions have a GWP of less than 650, e.g. less than 250.

The pharmaceutical solution of the present invention will typically comprise from 79.0 to 98.0 weight % of the propellant component, from 1.0 to 20.0 weight % of the ethanol and from 0.01 to 4.0 weight %, e.g. from 0.01 to 2.0 weight %, of the drug component. Preferred pharmaceutical solutions comprise from 87.0 to 98.0 weight % of the propellant component, from 1.0 to 12.0 weight % of the ethanol and from 0.01 to 2.0 weight % of the drug component. Especially preferred pharmaceutical solutions comprise from 93.0 to 98.0 weight % of the propellant component, from 1.0 to 6.0 weight % of the ethanol and from 0.01 to 2.0 weight % of the drug component. All percentages are based on the total weight of the pharmaceutical solution.

Although the drug component may comprise a mixture of beclomethasone dipropionate (BDP) and fluticasone propionate (FP), ordinarily the pharmaceutical solution will comprise just one of the drugs.

The pharmaceutical solutions of the invention may comprise one or more other additives of the type that are conventionally used in drug formulations for pressurised MDIs, such as valve lubricants. Where other additives are included in the pharmaceutical composition, they are normally used in amounts that are conventional in the art.

The pharmaceutical solution of the present invention will preferably consist essentially of and more preferably will consist entirely of the specified drug component, the specified propellant component and ethanol.

Accordingly, in a preferred embodiment the present invention provides a pharmaceutical solution for a medication delivery apparatus, especially a metered dose inhaler, which consists essentially of:
(a) a liquefied propellant component consisting essentially of and preferably consisting entirely of 1,1-difluoroethane (R-152a);
(b) ethanol; and
(c) a drug component dissolved in the propellant/ethanol mixture consisting of at least one drug selected from the group consisting of beclomethasone dipropionate (BDP) and fluticasone propionate (FP).

As used in relation to the propellant component, the term "consisting essentially of" has the meaning ascribed above.

In stating that the pharmaceutical solution consists essentially of the three specified components (a), (b) and (c) listed above, we mean that at least 95 weight %, more preferably at least 98 weight % and especially at least 99 weight % of the pharmaceutical solution is made up of components (a), (b) and (c). In a particularly preferred embodiment, the entirety of the pharmaceutical solution is made up of the three components (a), (b) and (c).

The pharmaceutical solutions of the present invention are preferably packaged in a suitable container, such as a pressurised aerosol canister, which can be used in association with a drug delivery device, such as a MDI, to deliver the composition to a patient.

Accordingly, the present invention also provides a pressurised aerosol canister comprising a pharmaceutical solution as discussed above. In a preferred embodiment, the aerosol canister is for use with a MDI.

The present invention also provides a MDI comprising a pressurised aerosol canister containing a pharmaceutical solution as discussed above.

The pharmaceutical solutions of the present invention are for use in medicine for treating a patient suffering or likely to suffer from a respiratory disorder and especially asthma or a chronic obstructive pulmonary disease.

Accordingly, the present invention also provides a method for treating a patient suffering or likely to suffer from a respiratory disorder which comprises administering to the patient a therapeutically or prophylactically effective amount of a pharmaceutical solution as discussed above. The respiratory disorder may be asthma or a chronic obstructive pulmonary disease. The pharmaceutical solution is preferably delivered to the patient using a MDI.

The pharmaceutical solutions of the invention can be prepared by a simple blending operation in which the R-152a propellant, the drug and the ethanol are mixed together in the required proportions in a suitable mixing vessel. Mixing can be promoted by stirring as is common in the art. Conveniently, the R-152a propellant is liquefied to aid mixing. If the pharmaceutical solution is made in a separate mixing vessel, it can then be transferred to pressurised containers for storage, such as pressurised containers that are used as part of medication delivery devices and especially MDIs.

The pharmaceutical solutions of the invention can also be prepared within the confines of a pressurised container, such as an aerosol canister or vial, from which the solutions are ultimately released as an aerosol spray using a medication delivery device, such as a MDI. In one version of this method, a weighed amount of the drug is introduced into the open container. A valve is then crimped onto the container and a liquid premix of the R-152a propellant and ethanol introduced through the valve into the container under pressure, optionally after first evacuating the container through the valve. The whole mixture can then be treated to dissolve the drug in the propellant/ethanol mixture, e.g. by vigorous shaking or using an ultrasonic bath. In another version of this method, a weighed amount of the drug and the required amount of ethanol are introduced into the open container. A valve is then crimped onto the container, optionally after mixing the drug and ethanol together, and the liquid R-152a propellant introduced through the valve into the container under pressure, optionally after first evacuating the container through the valve. The whole mixture can then be treated to dissolve the drug in the propellant/ethanol mixture, e.g. by vigorous shaking or using an ultrasonic bath. Suitable canisters may be made of plastics, metal or glass.

The canister may be filled with enough of the pharmaceutical solution to provide for a plurality of dosages. The pressurized aerosol canisters that are used in MDIs, typically contain 50 to 200 individual dosages.

The present invention is now illustrated but not limited by the following Examples.

Example 1

A pressure solubility apparatus was constructed in order to determine the solubility profiles of beclomethasone dipropionate (BDP) and fluticasone propionate (FP) in 1,1-difluoroethane (R-152a) and 1,1,1,2-tetrafluoroethane (R-134a).

An excess of active pharmaceutical ingredient was placed into a pressure cylinder (300 $cm^3$ stainless steel cylinder from Whitey, Inc.). A vacuum was applied to the cylinder, which was then chilled using liquid nitrogen. Approximately 80 grams of either R-152a or R-134a propellant was charged into the cylinder, which was then stored at 20° C. for 24 hours.

A filtration unit comprising a 15 µm filter in-line with a 5 µm filter was connected to the cylinder containing the excess of drug in propellant. A second receiver pressure cylinder (150 $cm^3$ stainless steel cylinder from Whitey, Inc.) was exposed to a vacuum and chilled using liquid nitrogen, which was then connected to the filtration unit. Approximately 30 grams of liquid propellant containing drug in excess was passed through the filtration unit and collected in the receiver pressure cylinder.

A modified piece of 3.2 mm (⅛") tubing was connected to the end of the receiver pressure cylinder, which was then attached to the stem of a continuous valve crimped on to a glass bottle. The 3.2 mm (⅛") tubing was used to depress the stem of the valve and therefore, enable the contents of the receiver pressure cylinder to be collected in the glass bottle. The glass bottle was weighed, following which one actuation was shot into a dose content uniformity apparatus (DUSA) connected to a vacuum pump operated at 30 L/min. The glass bottle was re-weighed and the mass of drug collected in the DUSA was determined by high performance liquid chromatography (HPLC).

This procedure was repeated (n=3) for each drug and propellant combination.

HPLC was used to determine drug content. The HPLC consisted of a pump, column oven, column coupled to a UV detector (all Agilent 1200, Wokingham Berkshire, UK). A Hypersil BDS C18 column (Fisher, Loughborough, UK, 5 µm, 250×4.6 mm i.d.) was used for high-throughput analysis of samples. The chromatographic conditions for each drug are provided in Table 1.

TABLE 1

Contract samples analysed

| Drug | Pump Flow Rate (ml · min⁻¹) | Mobile Phase | UV Wavelength (nm) | Column Temperature (° C.) |
|---|---|---|---|---|
| Beclomethasone Dipropionate (BDP) | 1.5 | 45% v/v methanol, 35% v/v acetonitrile and 20% v/v water | 222 | 40 |
| Fluticasone Propionate (FP) | 1.5 | 45% v/v methanol, 35% v/v acetonitrile and 20% v/v water | 235 | 40 |

The solubility of beclomethasone dipropionate (BDP) was analysed. The mean drug solubility (μg/g, ±Standard Deviation, S.D.) was found to be 179.98±5.23 in a propellant comprising 100% R-152a, compared to a mean drug solubility of 26.65±0.08 in a propellant comprising 100% R-134a.

Example 2

The solubility of fluticasone propionate (FP) was assessed according to the protocol described in Example 1. The mean drug solubility was found to be 73.55±3.98 in a propellant comprising 100% R-152a, compared to a solubility of 14.27±1.66 in a propellant comprising 100% R-134a.

Example 3

An experiment was conducted to determine the amount of ethanol required to dissolve an amount of fluticasone propionate in a R-152a/ethanol mixture equivalent to that which would give rise to a 50 μg dose of the drug on delivery from a MDI.

A series of glass vials were charged with 0.00869 g (8.69 mg) of fluticasone propionate. R-152a propellant was then added to each vial, the amount being decreased from one vial to the next to compensate for increasing amounts of ethanol. An amount of ethanol was then added to each vial, with the amount being increased in increments from one vial to the next, in order to determine the minimum amount of ethanol required to dissolve the fluticasone propionate in the R-152a/ethanol mixture. The combined amounts of R-152a propellant and ethanol were such that the amount of fluticasone propionate in the R-152a/ethanol mixture would give rise to a 50 μg dose of the drug on delivery from a MDI. The amount of ethanol in the R-152a/ethanol mixture was increased from 1% by weight on the total weight of the R-152a/ethanol mixture in 1% w/w increments. After adding the ethanol, each vial was sonicated in an effort to dissolve the drug, stored at 20° C. and then examined visually to determine whether the drug had in fact dissolved. The first clear solution gave us the amount of ethanol (% by weight on the total weight of the R-152a/ethanol mixture) required to achieve solubility at 20° C. It was determined that 5.0% w/w of ethanol was required to dissolve the fluticasone propionate.

Example 4

An experiment was conducted to determine the amount of ethanol required to dissolve an amount of beclomethasone dipropionate in a R-152a/ethanol mixture equivalent to that which would give rise to a 250 μg dose of the drug on delivery from a MDI.

A series of glass vials were charged with 0.039 g (39 mg) of beclomethasone dipropionate. R-152a propellant was then added to each vial, the amount being decreased from one vial to the next to compensate for increasing amounts of ethanol. An amount of ethanol was then added to each vial, with the amount being increased in increments from one vial to the next, in order to determine the minimum amount of ethanol required to dissolve the beclomethasone dipropionate in the R-152a/ethanol mixture. The combined amounts of R-152a propellant and ethanol were such that the amount of beclomethasone dipropionate in the R-152a/ethanol mixture would give rise to a 250 μg dose of the drug on delivery from a MDI. The amount of ethanol in the R-152a/ethanol mixture was increased from 1% by weight on the total weight of the R-152a/ethanol mixture in 1% w/w increments. After adding the ethanol, each vial was sonicated in an effort to dissolve the drug, stored at 20° C. and then examined visually to determine whether the drug had in fact dissolved. The first clear solution gave us the amount of ethanol (% by weight on the total weight of the R-152a/ethanol mixture) required to achieve solubility at 20° C. It was determined that 2.0% w/w of ethanol was required to dissolve the beclomethasone dipropionate.

Comparative Example 5

An experiment was conducted to determine the amount of ethanol required to dissolve an amount of fluticasone propionate in a R-134a/ethanol mixture equivalent to that which would give rise to a 50 μg dose of the drug on delivery from a MDI. Exactly the same procedure as described in Example 3 above was used except that R-134a was used as the propellant. It was determined that 13.0% w/w of ethanol (% by weight on the total weight of the R-134a/ethanol mixture) was required to dissolve the fluticasone propionate.

Comparative Example 6

An experiment was conducted to determine the amount of ethanol required to dissolve an amount of beclomethasone dipropionate in a R-134a/ethanol mixture equivalent to that which would give rise to a 250 μg dose of the drug on delivery from a MDI. Exactly the same procedure as described in Example 4 above was used except that R-134a was used as the propellant. It was determined that 4.0% w/w of ethanol (% by weight on the total weight of the R-134a/ethanol mixture) was required to dissolve the beclomethasone dipropionate.

Example 7

The in vitro aerosolization performance of fluticasone propionate and beclomethasone dipropionate in (i) a R152a/ethanol mixture and (ii) a R-134a/ethanol mixture was investigated. The fluticasone propionate solutions that were investigated were formulated to deliver a 50 μg dose of the drug. This equates to 0.83 mg of the drug per gram of liquid. The beclomethasone dipropionate solutions that were investigated were formulated to deliver a 250 μg dose of the drug. This equates to 3.71 mg of the drug per gram of liquid. The amount of ethanol used in each case was that required to dissolve the drug completely in the propellant/ethanol mixture.

Solution formulations of fluticasone propionate and beclomethasone dipropionate were prepared in R-152a/ethanol and R-134a/ethanol mixtures. The drug was weighed directly into standard aluminium 19 mL cans (C128, Presspart, Blackburn, UK), to which an appropriate amount of ethanol was added to aid solubility of the drug on addition of the propellant. The amount of ethanol included in the formulation for each drug is shown in Table 2. The slurry of the drug in ethanol was then sonicated for 60 minutes in order to disperse the drug in the ethanol. The cans were then crimped with a 504 valve (Bespak, Kings Lynn, UK) following which R-152a or R-134a as appropriate was filled into the cans through the valve using a manual Pamasol crimper/filler (Pamasol, Switzerland). Each can was then sonicated for 20 minutes to dissolve the drug. Finally, all the cans were quarantined for 14 days, valve down, at 22° C./44% RH before commencing testing of the final formulations.

TABLE 2

Ethanol content

| Drug | Ethanol Content in R-134a (% w/w) | Ethanol Content in R-152a (% w/w) |
| --- | --- | --- |
| Beclomethasone Dipropionate (BDP, 250 μg) | 4.0 | 2.0 |
| Fluticasone Propionate (FP, 50 μg) | 13.0 | 5.0 |

It is evident from Table 2 above that significantly less ethanol was required to dissolve the two drugs when R-152a was used as the propellant rather than R-134a.

High performance liquid chromatography (HPLC) was used to determine drug content following aerosolization studies (see below). The HPLC machine consisted of a pump, column oven, column coupled to a UV detector (all Agilent 1200, Wokingham, Berkshire, UK). A Hypersil BDS C18 column (Fisher, Loughborough, UK, 5 μm, 250×4.6 mm i.d.) was used. The chromatographic conditions for each drug are shown in Table 3.

TABLE 3

| Drug | Pump Flow Rate (ml·min$^{-1}$) | Mobile Phase | UV Wavelength (nm) | Column Temperature (° C.) |
| --- | --- | --- | --- | --- |
| Beclomethasone Dipropionate (BDP) | 1.5 | 45% v/v methanol, 35% v/v acetonitrile and 20% v/v water | 222 | 40 |
| Fluticasone Propionate (FP) | 1.5 | 45% v/v methanol, 35% v/v acetonitrile and 20% v/v water | 235 | 40 |

The in vitro aerosolization performance of each formulation was studied using a Next Generation Impactor (NGI, Copley Scientific, Nottingham UK), which was connected to a vacuum pump (GE Motors, NJ, USA). Prior to testing, the cups of the NGI system were coated with 1% v/v silicone oil in hexane to eliminate particle bounce. For each experiment, three actuations of the can were discharged into the NGI at 30 L·min$^{-1}$ as per pharmacopeia guidelines. Following aerosolization, the NGI apparatus was dismantled and the actuator and each part of the NGI was washed down into known volumes of the HPLC mobile phase. The mass of drug deposited on each part of the NGI was determined by HPLC. This procedure was repeated three times for each can, following which the emitted dose, the fine particle dose (FPD), the fine particle fraction of the emitted dose ($FPF_{ED}$), the mass median aerodynamic diameter (MMAD) and geometric standard deviation (GSD) were determined.

The in vitro aerosolization performance of the fluticasone propionate (50 μg) solutions prepared in (i) R152a and ethanol (5% w/w) and (ii) R-134a and ethanol (13% w/w) are summarised in Table 4 below and shown in FIG. 1.

TABLE 4

| Formulation | Emitted Dose (μg ± S.D.) | Fine Particle Dose (μg ± S.D.) | ($FPF_{ED}$) (%) | MMAD ± GSD |
| --- | --- | --- | --- | --- |
| R-134a/Ethanol (13.0% w/w) | 50.5 ± 1.8 | 20.6 ± 1.4 | 40.8 | 3.8 ± 4.2 |
| R-152a/Ethanol (5.0% w/w) | 49.5 ± 0.1 | 26.6 ± 1.8 | 53.7 | 3.2 ± 2.9 |

The emitted dose of the fluticasone propionate formulations prepared in R-134a/13.0% w/w ethanol and R-152a/5.0% w/w ethanol were similar. However, the fine particle dose and the fine particle fraction of the emitted dose were significantly (p<0.05) greater for the R-152a/ethanol formulation than for the R-134a/ethanol formulation. Furthermore, the mass median aerodynamic diameter of the formulation produced using R-152a and ethanol was smaller than that of the formulation produced using R-134a and ethanol.

The in vitro aerosolization performance of the beclomethasone dipropionate (250 μg) solutions prepared in (i) R152a and ethanol (2% w/w) and (ii) R-134a and ethanol (4% w/w) are summarised in Table 5 below and shown in FIG. 2.

TABLE 5

| Formulation | Emitted Dose (μg ± S.D.) | Fine Particle Dose (μg ± S.D.) | ($FPF_{ED}$) (%) | MMAD ± GSD |
| --- | --- | --- | --- | --- |
| R-134a/Ethanol (4.0% w/w) | 247.5 ± 0.5 | 122.3 ± 3.1 | 49.4 | 1.42 ± 2.12 |
| R-152a/Ethanol (2.0% w/w) | 250.2 ± 0.5 | 115.9 ± 0.2 | 46.3 | 1.49 ± 2.10 |

The emitted dose of the beclomethasone dipropionate formulations prepared in R-134a/4.0% w/w ethanol and R-152a/2.0% w/w ethanol were similar. The fine particle dose and the fine particle fraction of the emitted dose were greater for the R-134a/ethanol formulation than for the R-152a/ethanol formulation. However, the R-134a/ethanol formulation required twice as much ethanol to dissolve the beclomethasone dipropionate. The mass median aerodynamic diameter of the two formulations were also similar.

It is evident from the above aerosolization studies that less ethanol is needed to dissolve both fluticasone propionate and beclomethasone dipropionate when R-152a is used as the propellant rather than R-134a. This is an important advantage. In addition, the formulations that use R-152a exhibit useful aerosolization performance. Indeed, when fluticasone propionate is used as the drug, better aerosolization performance is achieved when R-152a is used as the propellant rather than R-134a.

The invention claimed is:

1. A pharmaceutical solution for delivery using a medication delivery apparatus to treat a respiratory disorder comprising:
   (a) a liquefied propellant component wherein the liquefied propellant component is 1,1-difluoroethan (R-152a);
   (b) 1.0 to 20.0 weight % of ethanol based on a total weight of the pharmaceutical solution; and
   (c) 0.01 to 4.0 weight % of a drug component dissolved in the pharmaceutical solution consisting of at least one drug selected from the group consisting of beclomethasone dipropionate (BDP) and fluticasone propionate (FP).

2. The pharmaceutical solution of claim 1, wherein at least 95 weight % of the solution is made up of components (a), (b) and (c).

3. The pharmaceutical solution of claim 2, wherein at least 98 weight % of the solution is made up of components (a), (b) and (c).

4. The pharmaceutical solution of claim 1, wherein the solution is made up entirely of components (a), (b) and (c).

5. The pharmaceutical solution of claim 1, wherein the drug component is beclomethasone dipropionate (BDP).

6. The pharmaceutical solution of claim 1, wherein the ethanol comprises from 1.0 to 6.0 weight % of the total weight of the pharmaceutical solution.

7. The pharmaceutical solution of claim 1 which comprises from 93.0 to 98.0 weight % of the propellant component, from 1.0 to 6.0 weight % of the ethanol and from 0.01 to 2.0 weight % of the drug component.

8. A sealed container that contains a pharmaceutical solution as claimed in claim 1.

9. A method for treating a patient suffering responsive to BDP or FP which comprises administering to the patient a therapeutically or prophylactically effective amount of a pharmaceutical solution as claimed in claim 1.

10. The pharmaceutical solution of claim 1, wherein the drug component is fluticasone propionate (FP).

11. The pharmaceutical solution of claim 2, wherein at least 99 weight % of the solution is made up of components (a), (b) and (c).

12. The pharmaceutical solution of claim 1, wherein the ethanol comprises from 1.0 to 12.0 weight % of the total weight of the pharmaceutical solution.

13. A pharmaceutical solution for delivery using a medication delivery apparatus to treat a respiratory disorder comprising:
   (a) a liquefied propellant component consisting essentially of 1,1-difluoroethane (R-152a);
   (b) 1.0 to 20.0 weight % of ethanol based on a total weight of the pharmaceutical solution; and
   (c) 0.01 to 4.0 weight % of a drug component dissolved in the pharmaceutical solution consisting of at least one drug selected from the group consisting of beclomethasone dipropionate (BDP) and fluticasone propionate (FP).

* * * * *